(12) United States Patent
Bai et al.

(10) Patent No.: US 11,499,956 B2
(45) Date of Patent: Nov. 15, 2022

(54) METHOD FOR ESTIMATING SOIL ORGANIC CARBON IN KARST AREA

(71) Applicant: Institute of Geochemistry, Chinese Academy of Sciences, Guiyang (CN)

(72) Inventors: Xiaoyong Bai, Guiyang (CN); Shijie Wang, Guiyang (CN); Luhua Wu, Guiyang (CN); Miao Zhou, Guiyang (CN); Fei Chen, Guiyang (CN); Huiwen Li, Guiyang (CN); Yue Cao, Guiyang (CN); Jianyong Xiao, Guiyang (CN); Qinghuan Qian, Guiyang (CN); Cheng Zeng, Guiyang (CN); Qin Li, Guiyang (CN); Jinfeng Wang, Guiyang (CN); Yichao Tian, Guiyang (CN); Guangjie Luo, Guiyang (CN); Yujie Yang, Guiyang (CN); Chaojun Li, Guiyang (CN); Yuanhong Deng, Guiyang (CN); Zeyin Hu, Guiyang (CN)

(73) Assignee: Institute of Geochemistry, Chinese Academy of Sciences, Guiyang (CN)

( * ) Notice: Subject to any disclaimer, the term of this patent is extended or adjusted under 35 U.S.C. 154(b) by 293 days.

(21) Appl. No.: 16/884,714

(22) Filed: May 27, 2020

(65) Prior Publication Data
US 2020/0408731 A1 Dec. 31, 2020

(30) Foreign Application Priority Data
Jun. 28, 2019 (CN) .......................... 201910576376.X

(51) Int. Cl.
*G01N 33/24* (2006.01)
*G06F 30/17* (2020.01)

(52) U.S. Cl.
CPC ............. *G01N 33/24* (2013.01); *G06F 30/17* (2020.01)

(58) Field of Classification Search
CPC ............................... G01N 33/24; G06F 30/17
See application file for complete search history.

(56) References Cited

FOREIGN PATENT DOCUMENTS

| CN | 105699624 A | * | 6/2016 | |
|---|---|---|---|---|
| CN | 112782385 A | * | 5/2021 | |
| CN | 113176393 A | * | 7/2021 | |
| WO | WO-2011150472 A1 | * | 12/2011 | ............. G01N 33/24 |

* cited by examiner

*Primary Examiner* — Ryan D Walsh
(74) *Attorney, Agent, or Firm* — Dority & Manning, P.A.

(57) ABSTRACT

The present invention discloses a method for estimating soil organic carbon in karst area, including: step 1, establishing a soil organic carbon estimation model for the karst area; step 2, revising a soil depth; step 3, subtracting an exposure rate of bedrock for different types of soil and positive and negative terrains; step 4, revising a soil organic carbon density estimation formula for different types of soil and positive and negative terrains; and step 5, revising a soil organic carbon storage estimation method. This invention has solved the problem of overestimating soil organic carbon pool by existing methods, has improved the calculation accuracy, and has promoted the research process of soil carbon cycle in karst area.

1 Claim, No Drawings

METHOD FOR ESTIMATING SOIL ORGANIC CARBON IN KARST AREA

The present application claims priority to Chinese Patent Application No. 201910576376.X, filed with the China National Intellectual Property Administration on Jun. 28, 2019, which is incorporated herein by reference in its entirety.

TECHNICAL FIELD

The present invention belongs to the field of calculation of soil carbon content in karst area, and particularly relates to a method for estimating soil organic carbon in karst area.

BACKGROUND

In karst area, the soil is shallow and unevenly distributed due to the high exposed rate of bedrock and broken surface An in-depth understanding of the spatial distribution characteristics of soil organic carbon density and storage directly relates to ecological restoration and reconstruction planning of karst rocky desertification areas. It has a significant impact on the recommendations and decisions of construction of ecological civilization, and poses a great significance to ensure the ecological security of the Yangtze River and Pearl River basins. However, in the horizontal direction, the existing methods for estimating soil organic carbon density cannot truly reflect the characteristics of karst soil, don't take into account the characteristics of soil forming rate, distribution and erosion of karst soil, and also ignores the significant impact of bedrock exposure rate. In a vertical direction, these existing methods don't consider the actual depth of soil, which leads to a large calculation error that the estimated soil carbon pool in karst area is much higher than the actual situation.

SUMMARY

A technical problem to be solved by the present invention is: to provide a method for estimating soil organic carbon in karst area, so as to solve the technical problems of the prior art that when soil organic carbon in karst area is calculated, a karst soil carbon pool is calculated to be significantly higher than the actual situation, and a large calculation error occurs, etc.

The present invention has a technical solution as follows:

A method for estimating soil organic carbon in karst area, including:

step 1, establishing a soil organic carbon estimation model for the karst area;

step 2, revising a soil depth;

step 3, subtracting an exposure rate of bedrock for different types of soil and positive and negative terrains;

step 4, revising a soil organic carbon density estimation formula for different types of soil and positive and negative terrains; and step 5, revising a soil organic carbon storage estimation method.

In the step 1, the soil organic carbon estimation model established for the karst area is:

$$SOCS = \sum_{i=1}^{k} SOCD_i \times S_i \times 10^3$$

-continued
$$SOCD_i = SOCD_{non-karst} + SOCD_{karst}$$

$$SOCD_{karst} = SOCD_{non-limestone\ soil\ type\ below\ 6°} + SOCD_{limestone\ soil\ type\ below\ 6°} + SOCD_{all\ soil\ types\ above\ 6°}$$

$$SOCD_{non-karst} = \sum_{i=1}^{k} C_i D_i E_i (1 - G_i)/10$$

where: SOCS is soil organic carbon storage (g C), $SOCD_i$ is an organic carbon density (kg/m$^2$), $SOCD_{non-karst}$ is an organic carbon density in non-karst area (kg/m$^2$), $SOCD_{karst}$ is an organic carbon density in karst area (kg/m$^2$), $SOCD_{non-limestone\ soil\ below\ 6°}$ is an organic carbon density in limestone soil type areas below 6°, $SOCD_{limestone\ soil\ below\ 6°}$ is an organic carbon density in limestone soil type areas below 6° (kg/m$^2$), $SOCD_{all\ soil\ types\ above\ 6°}$ is an organic carbon density in all soil types areas above 6° (kg/m$^2$), $C_i$ is the soil organic carbon content (%), $D_i$ is the soil bulk density (g/cm$^3$), $E_i$ is the soil thickness (cm) (1 m for a non-karst area), $G_i$ is the content of a gravel greater than 2 mm (%), $S_i$ is a pixel area (m$^2$), i is a pixel number, and k is the total number of pixels.

In the step 2, the method for revising a soil depth is: using an actual soil depth $E_i$ as the soil depth of the positive and negative terrains and any soil types.

In the step 3, the method for subtracting an exposure rate of bedrock for different types of soil and positive and negative terrains is: determining that the exposure rate $R_i$ of bedrock for a non-limestone soil type in a negative terrain below 6° is 0, and using an actual exposure rate $R_i$ of bedrock for a non-limestone soil type below 6° and all soil types of a positive terrain above 6°.

The soil organic carbon density estimation formula revised for different types of soil and positive and negative terrains includes:

A calculation formula of $SOCD_{non-limestone\ soil\ below\ 6°}$ is as follows:

$$SOCD_{non-limestone\ soil\ type\ below\ 6°} = \sum_{i=1}^{k} C_i D_i E_i (1 - G_i)/10$$

where, $SOCD_{non-limestone\ soil\ below\ 6°}$ is an organic carbon density in limestone soil type areas below 6° (kg/m$^2$); $C_i$ is a soil organic carbon content (%); $D_i$ is a soil bulk density (g/cm$^3$); $E_i$ is an actual soil thickness in a karst area (cm) (0≤$E_i$≤1 m), rather than 1 m used in a traditional formula; $G_i$ is the content of a gravel greater than 2 mm (%); i is a pixel number; and k is the total number of pixels.

Calculation formulas of $SOCD_{limestone\ soil\ type\ below\ 6°}$ and $SOCD_{all\ soil\ types\ above\ 6°}$ are respectively as follows:

$$SOCD_{limestone\ soil\ type\ below\ 6°} = \sum_{i=1}^{k} C_i D_i E_i (1 - G_i)/10 \times (1 - R_i)$$

$$SOCD_{all\ soil\ types\ above\ 6°} = \sum_{i=1}^{k} C_i D_i E_i (1 - G_i)/10 \times (1 - R_i)$$

where, $SOCD_{limestone\ soil\ below\ 6°}$ is an organic carbon density in limestone soil type areas below 6° (kg/m$^2$), $SOCD_{all\ soil\ types\ above\ 6°}$ is an organic carbon density in all soil types areas above 6° (kg/m$^2$), $C_i$ is a soil organic carbon content (%); $D_i$ is a soil bulk density (g/cm³); $E_i$ is an actual soil thickness in a karst area (cm) ($0 \leq E_i \leq 1$ m), rather than 1 m used in a traditional formula; $G_i$ is the content of a gravel greater than 2 mm (%); $R_i$ is the exposure rate of soil bedrock (%), i is a pixel number; and k is the total number of pixels.

$$SOCS = \sum_{i}^{k} SOCD_i \times S_i \times 10^3$$

$$= \sum_{i=1}^{k} (SOCD_{non-karst} + SOCD_{karst}) \times S_i \times 10^3$$

$$= \sum_{i=1}^{k} (SOCD_{non-limestone\ soil\ type\ below\ 6°} +$$

$$SOCD_{limestone\ soil\ type\ below\ 6°} +$$

$$SOCD_{all\ soil\ types\ above\ 6°}) \times S_i \times 10^3$$

$$= (\sum_{i=1}^{k} (C_i D_i E_i (1 - G_i)/10 +$$

$$\sum_{i=1}^{k} C_i D_i E_i (1 - G_i)/10 \times$$

$$(1 - R_i)) \times S_{i,j} \times 10^3$$

In the step 5, the revised soil organic carbon storage estimation method includes: where, SOCS is soil organic carbon storage (g C), $SOCD_i$ is an organic carbon density (kg/m²), $SOCD_{non-karst}$ is an organic carbon density in non-karst area (kg/m²), $SOCD_{karst}$ is an organic carbon density in karst area (kg/m²), $SOCD_{non-limestone\ soil\ below\ 6°}$ is an organic carbon density in limestone soil type areas below 6°, $SOCD_{limestone\ soil\ below\ 6°}$ is an organic carbon density in limestone soil type areas below 6° (kg/m²), $SOCD_{all\ soil\ types\ above\ 6°}$ is an organic carbon density in all soil types areas above 6° (kg/m²), $C_i$ is the soil organic carbon content (%), $D_i$ is the soil bulk density (g/cm³), $E_i$ is the soil thickness (cm) (1 m for a non-karst area), $G_i$ is the content of a gravel greater than 2 mm (%), $S_i$ is a pixel area (m²), i is a pixel number, and k is the total number of pixels.

The present invention has the following beneficial effects.

The present invention proposes a soil organic carbon storage calculation model suitable for a karst mountain-dam coupled system, which revises a soil depth, subtracts an exposure rate of bedrock for different types of soil and positive and negative terrains, revises a soil organic carbon density estimation formula for different types of soil and positive and negative terrains, and finally obtains a new soil organic carbon storage estimation method. In a horizontal direction, an exposure parameter of bedrock is introduced, which eliminates the significant influence of an exposure rate of bedrock. In a vertical direction, the spatial heterogeneity of the actual soil depth is considered. In addition, according to the soil types and the characteristics of slope, the carbon density of non-limestone soil type below 6°, limestone soil type below 6° and all soil type areas above 6° is calculated separately. For the non-limestone soil type below 6°, it is not necessary to consider the exposure rate of bedrock; for the limestone soil type below 6° and all soil type areas above 6°, it is necessary to consider the exposure rate of bedrock. Compared with a traditional algorithm, the new method and model established by the present invention for estimating soil organic carbon storage in karst area solve the problem that a traditional model is difficult to apply to a complex karst mountain-dam coupled system, and provides a new scientific method for the research and estimation of soil organic carbon distribution characteristics in a karst watershed, provides a technical support and scientific theoretical basis for the ecological restoration and reconstruction of karst areas in China, provides an important reference for the decision-making and overall arrangement of ecological civilization construction in the southwestern region, improves the accuracy of calculation, and solves the technical problems of the prior art that when soil organic carbon in karst area is calculated, a karst soil carbon pool is calculated to be significantly higher than the actual situation, and a large calculation error occurs, etc.

DETAILED DESCRIPTION

The method provided by the present invention includes the following steps:

a method for estimating soil organic carbon in karst area, including:

step 1, establish a soil organic carbon estimation model for the karst area;

step 2, revise a soil depth;

step 3, subtract an exposure rate of bedrock for different types of soil and positive and negative terrains;

step 4, revise a soil organic carbon density estimation formula for different types of soil and positive and negative terrains; and step 5, revise a soil organic carbon storage estimation method.

In the step 1, the calculation is carried out by using the following method:

$$SOCS = \sum_{i=1}^{k} SOCD_i \times S_i \times 10^3$$

$$SOCD_i = SOCD_{non-karst} + SOCD_{karst}$$

$$SOCD_{karst} = SOCD_{non-limestone\ soil\ type\ below\ 6°} +$$

$$SOCD_{limestone\ soil\ type\ below\ 6°} + SOCD_{all\ soil\ types\ above\ 6°}$$

$$SOCD_{non-karst} = \sum_{i=1}^{k} C_i D_i E_i (1 - G_i)/10$$

where, SOCS is soil organic carbon storage (g C), $SOCD_i$ is an organic carbon density (kg/m²), $SOCD_{non-karst}$ is an organic carbon density in non-karst area (kg/m²), $SOCD_{karst}$ is an organic carbon density in karst area (kg/m²), $SOCD_{non-limestone\ soil\ below\ 6°}$ is an organic carbon density in limestone soil type areas below 6°, $SOCD_{limestone\ soil\ below\ 6°}$ is an organic carbon density in limestone soil type areas below 6° (kg/m²), $SOCD_{all\ soil\ types\ above\ 6°}$ is an organic carbon density in all soil types areas above 6° (kg/m²), $C_i$ is a soil organic carbon content (%), $D_i$ is a soil bulk density (g/cm³), $E_i$ is a soil thickness (cm) (1 m for a non-karst area), $G_i$ is the content of a gravel greater than 2 mm (%), $S_i$ is a pixel area (m²), i is a pixel number, and k is the total number of pixels.

In the step 2, the positive and negative terrains and any soil types all should consider the actual soil depth $E_i$ (cm) ($0 \leq E_i \leq 1$ m), rather than following a previous 1 m standard suitable for a non-karst area.

In the step 3, the exposure rate $R_i$ of bedrock for a non-limestone soil type below 6° (negative terrain) is 0. A non-limestone soil type below 6° and all soil types above 6° (positive terrain) all should consider an actual exposure rate $G_i$ of bedrock.

A calculation formula of $SOCD_{non-limestone\ soil\ type\ below\ 6°}$ is:

$$SOCD_{non-limestone\ soil\ type\ below\ 6°} = \sum_{i=1}^{k} C_i D_i E_i (1 - G_i)/10$$

where, $SOCD_{non-limestone\ soil\ below\ 6°}$ is organic carbon density in limestone soil type areas below 6° (kg/m²); $C_i$ is a soil organic carbon content (%); $D_i$ is a soil bulk density (g/cm³); $E_i$ is an actual soil thickness in a karst area (cm) (0≤$E_i$≤1 m), rather than 1 m used in a traditional formula; $G_i$ is the content of a gravel greater than 2 mm (%); i is a pixel number; and k is the total number of pixels.

The calculation formulas of $SOCD_{limestone\ soil\ type\ below\ 6°}$ and $SOCD_{all\ soil\ types\ above\ 6°}$ are respectively as follows:

$$SOCD_{limestone\ soil\ type\ below\ 6°} = \sum_{i=1}^{k} C_i D_i E_i (1 - G_i)/10 \times (1 - R_i)$$

$$SOCD_{all\ soil\ types\ above\ 6°} = \sum_{i=1}^{k} C_i D_i E_i (1 - G_i)/10 \times (1 - R_i)$$

where, $SOCD_{limestone\ soil\ below\ 6°}$ is an organic carbon density in limestone soil type areas below 6° (kg/m²), $SOCD_{all\ soil\ types\ above\ 6°}$ is an organic carbon density in all soil types areas above 6° (kg/m²), $SOCD_i$ is an organic carbon density (kg/m²), $C_i$ is a soil organic carbon content (%), $D_i$ is a soil bulk density (g/cm³), $E_i$ is a soil thickness (cm) (0≤$E_i$≤1 m), $G_i$ is the content of a gravel greater than 2 mm (%), $R_i$ is an exposure rate of soil bedrock (%), i is a pixel number, and k is the total number of pixels.

In the step 5, a soil organic carbon storage estimation method is revised, and the calculation is carried out by using the following method:

$$\begin{aligned}SOCS &= \sum_{i}^{k} SOCD_i \times S_i \times 10^3 \\ &= \sum_{i=1}^{k} (SOCD_{non-karst} + SOCD_{karst}) \times S_i \times 10^3 \\ &= \sum_{i=1}^{k} (SOCD_{non-limestone\ soil\ type\ below\ 6°} + \\ &\quad SOCD_{limestone\ soil\ type\ below\ 6°} + \\ &\quad SOCD_{all\ soil\ types\ above\ 6°}) \times S_i \times 10^3\end{aligned}$$

where, SOCS is organic carbon storage (g C), $SOCD_i$ is an organic carbon density (kg/m²), $SOCD_{non-karst}$ is an organic carbon density in non-karst area, $SOCD_{karst}$ is an organic carbon density in karst area, $SOCD_{non-limestone\ soil\ below\ 6°}$ is an organic carbon density in limestone soil type areas below 6°, $SOCD_{limestone\ soil\ below\ 6°}$ is an organic carbon density in limestone soil type areas below 6°, $SOCD_{all\ soil\ types\ above\ 6°}$ is an organic carbon density in all soil types areas above 6°, $S_i$ is a pixel area (m²), i is a pixel number, and k is the total number of pixels.

The method of the present invention is aimed at solving the problem of misjudgment in carbon pool estimation due to the lack of a systematic understanding of the actual spatial distribution features of soil in karst area with high exposure rate of bedrock and shallow soil, and the method considers the heterogeneity of soil depth in the karst area, and uses an actual soil depth $E_i$ to replace the soil thickness E (1 m) in a general formula. In addition, the carbon density of non-limestone soil below 6°, limestone soil type below 6° and all areas above 6° is calculated separately. For the non-limestone soil type below 6°, it is not necessary to consider the exposure rate of bedrock; for the limestone soil type below 6° and all soil type areas above 6°, it is necessary to consider the exposure rate of bedrock. The method eliminates the exposure rate of bedrock and considers the actual soil depth to establish a new method and model for estimating soil organic carbon storage in karst area, which solves the problems of the prior art and improves the calculation accuracy.

What is claimed is:

1. A method for ecological restoration and reconstruction of a karst area, comprising:

step 1: acquiring, by measuring, parameters of karst soil in the karst area;

step 2: establishing a soil organic carbon storage estimation model for the karst area, wherein the soil organic carbon storage estimation model for the karst area is:

$$SOCS = \sum_{i=1}^{k} SOCD_i \times S_i \times 10^3,$$

where $SOCD_i = SOCD_{non-karst} + SOCD_{karst}$, $SOCD_{karst} = SOCD_{non-limestone\ soil\ type\ below\ 6°} + SOCD_{limestone\ soil\ type\ below\ 6°} + SOCD_{all\ soil\ types\ above\ 6°}$, and $$SOCD_{non-karst} = \sum_{i=1}^{k} C_i D_i E_i (1 - G_i)/10$$

wherein SOCS is a soil organic carbon storage (g C), $SOCD_i$ is an organic carbon density (kg/m²), $SOCD_{non-karst}$ is an organic carbon density in a non-karst area (kg/m²), $SOCD_{karst}$ is an organic carbon density in the karst area (kg/m²), $SOCD_{non-limestone\ soil\ below\ 6°}$ is an organic carbon density in limestone soil type areas below 6° (kg/m²), $SOCD_{limestone\ soil\ below\ 6°}$ is an organic carbon density in limestone soil type areas below 6° (kg/m²), $SOCD_{all\ soil\ types\ above\ 6°}$ is an organic carbon density in all soil types areas above 6° (kg/m²), $C_i$ is a soil organic carbon content (%), $D_i$ is a soil bulk density (g/cm³), $E_i$ is a soil depth (cm) (0≤$E_i$≤1 m), $G_i$ is a content of a gravel greater than 2 mm (%), $R_i$ is an exposure rate of soil bedrock (%), i is a pixel number, and k is a total number of pixels;

step 3: revising, based on an actual soil depth value from the measured parameters, a soil depth parameter in the soil organic carbon storage estimation model;

step 4: subtracting an exposure rate of bedrock for different types of soil, positive terrains and negative terrains in the soil organic carbon storage estimation model with the actual soil depth value, wherein subtracting the exposure rate of bedrock for different types of soil, the positive terrains and the negative terrains comprises: the exposure rate Ri of soil bedrock for a non-limestone soil type in the negative terrain below 6° is set as 0, and an actual exposure rate Ri of bedrock for a limestone soil type below 6° and all soil types of the positive terrains above 6°;

step 5: revising a soil organic carbon density using formulas for different types of soil, the positive terrains and the negative terrains in the soil organic carbon storage estimation model, wherein the formulas comprise:

a calculation formula of $SOCD_{non\text{-}limestone\ soil\ below\ 6°}$ is as follows:

$$SOCD_{non\text{-}limestone\ soil\ type\ below\ 6°} = \sum_{i=1}^{k} C_i D_i E_i (1-G_i)/10$$

wherein, $SOCD_{non\text{-}limestone\ soil\ below\ 6°}$ is an organic carbon density in limestone soil type areas below 6° (kg/m$^2$), $C_i$ is the soil organic carbon content (%), $D_i$ is the soil bulk density (g/cm$^3$), $E_i$ is the soil thickness (cm) (0≤$E_i$≤1 m), $G_i$ is a content of a gravel greater than 2 mm (%), $R_i$ is the exposure rate of soil bedrock (%), i is a pixel number, and k is the total number of pixels; and calculation formulas of $SOCD_{limestone\ soil\ below\ 6°}$ and $SOCD_{all\ soil\ types\ above\ 6°}$ are respectively as follows:

$$SOCD_{limestone\ soil\ type\ below\ 6°} = \sum_{i=1}^{k} C_i D_i E_i (1-G_i)/10 \times (1-R_i)$$

$$SOCD_{all\ soil\ types\ above\ 6°} = \sum_{i=1}^{k} C_i D_i E_i (1-G_i)/10 \times (1-R_i)$$

wherein, $SOCD_{limestone\ soil\ below\ 6°}$ is an organic carbon density in limestone soil type areas below 6° (kg/m$^2$), $SOCD_{all\ soil\ types\ above\ 6°}$ is an organic carbon density in all soil types areas above 6° (kg/m$^2$), $C_i$ is soil organic carbon content (%), $D_i$ is a soil bulk density (g/cm$^3$), $E_i$ is a soil thickness (cm) (0≤$E_i$≤1 m), $G_i$ is a content of a gravel greater than 2 mm (%), $R_i$ is an exposure rate of soil bedrock (%), i is a pixel number, and k is the total number of pixels;

step 6: obtaining the revised soil organic carbon storage from the soil organic carbon storage estimation model; and step 7: restoring and reconstructing the karst area based on the obtained soil organic carbon storage.

\* \* \* \* \*